United States Patent
Bobbert

(10) Patent No.: US 10,154,950 B2
(45) Date of Patent: Dec. 18, 2018

(54) ANTIMICROBIAL COMPOSITIONS CONTAINING LOW CONCENTRATIONS OF FOOD ALLOWED ORGANIC ACIDS AND AMINE OXIDE AMPHOTERIC SURFACTANTS

(71) Applicant: HYGIENIX BV, AT Hilversum (NL)

(72) Inventor: Ilja Bobbert, AT Hilversum (NL)

(73) Assignee: HYGIENIX BV, Hilversum (NL)

( * ) Notice: Subject to any disclaimer, the term of this patent is extended or adjusted under 35 U.S.C. 154(b) by 0 days.

(21) Appl. No.: 15/106,651

(22) PCT Filed: Dec. 19, 2014

(86) PCT No.: PCT/EP2014/078690
§ 371 (c)(1),
(2) Date: Jun. 20, 2016

(87) PCT Pub. No.: WO2015/091925
PCT Pub. Date: Jun. 25, 2015

(65) Prior Publication Data
US 2017/0000706 A1 Jan. 5, 2017

(30) Foreign Application Priority Data
Dec. 19, 2013 (EP) .................................... 13198433

(51) Int. Cl.
| | | |
|---|---|---|
| *A61K 8/365* | (2006.01) | |
| *A01N 25/30* | (2006.01) | |
| *A61K 8/362* | (2006.01) | |
| *A61K 8/44* | (2006.01) | |
| *A61Q 19/00* | (2006.01) | |
| *A61Q 19/10* | (2006.01) | |

(52) U.S. Cl.
CPC .............. *A61K 8/365* (2013.01); *A01N 25/30* (2013.01); *A61K 8/362* (2013.01); *A61K 8/44* (2013.01); *A61Q 19/007* (2013.01); *A61Q 19/10* (2013.01); *A61K 2800/30* (2013.01)

(58) Field of Classification Search
CPC .......... A61K 8/365; A61K 8/362; A61K 8/44; A61Q 19/007
See application file for complete search history.

(56) References Cited

U.S. PATENT DOCUMENTS

| | | | | |
|---|---|---|---|---|
| 5,023,008 A | * | 6/1991 | Scardera ................. | C11D 3/48 106/18.32 |
| 5,990,064 A | | 11/1999 | Wierenga et al. | |
| 8,193,136 B2 | * | 6/2012 | Taylor ..................... | A61K 8/40 510/119 |
| 9,131,682 B2 | * | 9/2015 | Crider ..................... | A01N 25/30 |
| 2002/0002125 A1 | * | 1/2002 | Colurciello, Jr. ........ | C11D 1/62 510/238 |
| 2005/0101515 A1 | | 5/2005 | Pawson et al. | |
| 2013/0172415 A1 | | 7/2013 | Vermeulen et al. | |

FOREIGN PATENT DOCUMENTS

| | | |
|---|---|---|
| WO | 00/66079 A1 | 11/2000 |
| WO | 2007/100917 A2 | 9/2007 |
| WO | 2010/084057 A1 | 7/2010 |

OTHER PUBLICATIONS

Mar. 27, 2015 International Search Report issued in International Patent Application No. PCT/EP2014/078690.
Mar. 27, 2015 Written Opinion issued in International Patent Application No. PCT/EP2014/078690.

* cited by examiner

*Primary Examiner* — Shirley V Gembeh
(74) *Attorney, Agent, or Firm* — Oliff PLC

(57) ABSTRACT

The invention pertains to an antimicrobial disinfecting composition including: a) 0.1-1 wt. % of each of at least one food allowed organic acid or a salt thereof; b) 0.1-1 wt. % of each of at least one amine oxide amphoteric surfactant, the composition having a total surfactant content which does not exceed 8 wt. %, wherein the total amount of betaine amphoteric surfactants in the composition is in the range of 0-75 wt. % of the total amount of amine oxide amphoteric surfactant. The composition is particularly suitable for use on skin or mucous membranes. On the one hand it shows good disinfecting properties, but on the other hand it does not lead to any use precautions or hazard or warning statements on the product label.

20 Claims, No Drawings

ANTIMICROBIAL COMPOSITIONS CONTAINING LOW CONCENTRATIONS OF FOOD ALLOWED ORGANIC ACIDS AND AMINE OXIDE AMPHOTERIC SURFACTANTS

The present invention relates to highly efficacious antimicrobial formulations, containing only low levels of food allowed organic acids and low levels of amphoteric surfactants. The formulations can be used on skin, mucous membranes and hard surfaces. The invention also relates to a method to reduce a bacterial population by contacting a substrate with the composition.

Most antimicrobial hand wash and hard surface formulations exhibiting broad-spectrum activity contain surfactants and antimicrobially active ingredients. Surfactants are employed, in part, to help solubilize the dirt on skin and surfaces, to enhance wetting of surfaces and skin. The surfactants are typically selected from anionic, non-ionic, amphoteric, and cationic surfactants.

Antimicrobially active ingredients are generally of the groups of quaternary ammonium compounds, biguanides, phenols, triclosan, halogens, peroxides, etc. Halogens and peroxides have unfavorable safety profiles, or require safety precautions, when used in concentrations that are antimicrobially active, and often release (toxic) fumes and gasses (chlorine for example). In hard surface sanitizers and disinfectants most frequently quaternary ammonium compounds or polymeric biguanides are being used, which are recently both proven to cause microbial resistance because of their "sub-minimal inhibitory concentration" residual effect on surfaces. These compounds are increasingly under suspicion because of skin irritation, ecological toxicity, human toxicity and the fact that they induce resistance in microbes, including increased resistance against antibiotics.

With the safety profile of triclosan, quaternary ammonium compounds and biguanides being questioned and the clear cause of increasing resistance of microbes caused by these compounds, and the presence of pathogenic bacteria and outbreaks increasing, there exists a need for antibacterial products that are low in concentration of triclosan, quaternary ammonium compounds and biguanides, but still effective at killing microorganisms.

Food allowed organic acids are very environmentally friendly and non-suspicious active ingredients. They are frequently used in food to preserve food and often used in cleaners and hand washes to preserve compositions. The drawback of these ingredients is that they are required in relatively high concentrations to be antimicrobially active, while in these concentrations a product is required to carry hazard warnings with use-precautions on the product label. Often these acids are present in high single digit percentages, or even exceeding ten percent in formulations.

Frequently used in cleaning compositions are lactic acid and citric acid. Lactic acid, citric acid or salts thereof are generally present in liquid cleansing compositions. For example in US2013/0172415 A1, which discloses an antibacterially active hand sanitizer based on lactic acid, wherein the concentration of lactic acid is between 5% and 15%.

However, the high concentrations of organic acids in these antibacterial compositions results in hazard warnings and safety sentences under European CLP (Classification, labelling and packaging of substances and mixtures). Biocidal products, regulated under the Biocidal Products Regulation (BPR) in the European Union, are hazard classified under the European CLP guidelines and globally classified under the United Nations Globally Harmonised System of Classification and Labelling of Chemicals (GHS). The GHS is a United Nations system to identify hazardous chemicals and to inform users about these hazards through standard symbols and phrases on the packaging labels and through safety data sheets. Accordingly, exceeding a threshold of 1% of organic acid or 1% of most amphoteric surfactants will lead to a hazard classification and use precaution under CLP.

Antibacterially active cleaning compositions most frequently also require high levels of surfactants. Surfactants are selected from anionics, nonionics, cationics and amphoterics. Cationic surfactants are often antimicrobially active in themselves, but are in most cases not preferred because of their ecological and human toxicity profile and the antimicrobial resistance they cause.

Ionic surfactants have a hydrophobic part and a hydrophilic part. The hydrophobic part consists of an uncharged carbohydrate group that can be straight, branched, cyclic or aromatic. Anionic surfactants have a negative charge on their polar head group and cationic surfactants have a positive charge. Some surfactants have the potential to have both positive and negative charges depending on the environment they are placed. Surfactants of this type are called amphoterics. For the amphoteric surfactants the charge of the hydrophilic part is controlled by the pH of the solution. This means that they can act as anionic surfactant in an alkaline solution or as cationic surfactant in an acidic solution.

The use of amphoteric surfactants and most notably the amine oxide detergent surfactants in cleaning compositions is well known. Amphoteric surfactants are most commonly used as co-surfactants to boost and maintain suds formation in laundry, shampoo, and dishwashing detergent compositions. Amphoteric surfactants and especially amine oxides have occasionally been used in hard surface cleaners such as acidic toilet bowl cleaners (pH of 2 or less), dishwashing liquids containing occlusive emollients (pH of 4 to 6.9), and selected non-acidic (neutral to alkaline) hard surface cleaners. Generally the amphoteric or amine oxide is used at higher than neutral pH, in its non-ionic form, where it possesses good cleaning properties and good foam behavior. The major uses of amine oxides are in laundry and cleaning products, where they function as foam stabilizer, thickener, or emulsifying or conditioning agent.

U.S. Pat. No. 5,990,064 claims a cleaning composition containing between 1% and 60% amine oxide, an amine and optionally an anionic surfactant.

Application WO2010/084057 describes an antibacterially active composition (Table 5, page 12) comprising amine oxide and silver nitrate. The concentration of amine oxide is between 1 and 15% by weight.

It is an object of the present invention to provide a cleaning composition with a low concentration of traditional antimicrobially active compounds such as quaternary ammonium compounds, triclosan, or biguanides, but which still has a good cleaning ability and high antimicrobial activity, also after short contact times.

To build effective cleaning liquids or soaps, surfactants are required to enhance wetting and cleaning ability, as well as to regulate foaming behavior. In order for the biocidal product to be safe and non-hazard classified, the food tolerant organic acids should be combined with surfactants that are able to cause synergies with the acids. Both components need to be present at low concentrations.

These low concentrations are critical because of the desired safety profile of the product. A hazard classification prescribing to wear one or more of protective gloves, protective clothing, eye protection, or face protection while using the product is in reality impossible or at least highly unpractical for consumers. Washing hands with a product that requires the user to wear gloves because of a hazard qualification while handling and using the product is highly unrealistic. However, the low concentrations required to avoid such hazard classification create substantial challenges. The lower the concentration of active ingredients and surfactants, the less efficacious the product becomes. Also its cleaning ability and foaming behavior will substantially deteriorate. In order to boost efficacy and foaming behavior, a person skilled in the art would be tempted to increase the levels of both active ingredients and surfactants, thereby compromising the safety profile of the product and causing the product to be classified as a hazardous substance with use precautions under CLP or GHS.

Surprisingly, it has now been found that a delicate balance of certain organic acids and certain amphoteric surfactants at low concentrations results in highly antimicrobially active, well foaming and well cleaning, but non hazard classified products. These products are safe to use on multiple surfaces and on the human body. The skin irritation potential is very low, while the cleaning and foaming behavior is acceptable to very good.

The prior art describes compositions containing either organic acids, such as lactic acid or the use of certain amphoterics, such as amine oxides, but these compositions are only antimicrobially active when further antimicrobially active ingredients are added to the composition, such as quaternary ammonium compounds, phenols, silver compounds or triclosan. The antibacterial effect is derived from the additional ingredients. US2005/0101515 e.g. describes an antimicrobial liquid cleansing formulation comprising surfactant, an acid and at least one phospholipid. The antibacterial efficacy is provided by the combination of the synthetic phospholipid with the acid.

WO00/66079 discloses an antibacterial liquid hand soap comprising 0.25% to 5% of a zwitterionic surfactant, 5%-16% of at least one second surfactant (such as amine oxide) and 0.1%-4% of a of a hydroxyl containing organic acid. Though this composition has an acceptable organic acid level, the level of the second surfactant is high and the product will be hazard classified under CLP.

There is need in the art for a composition which on the one hand shows good disinfecting properties, but which on the other hand does not lead to any use precautions or hazard or warning statements on the product label. This problem has been solved by the present invention.

The present invention pertains to an antimicrobial disinfecting composition comprising:
a) 0.1-1 wt. % of each of at least one food allowed organic acid or a salt thereof;
b) 0.1-1 wt. % of each of at least one amine oxide amphoteric surfactant,
the composition having a total surfactant content which does not exceed 8 wt. %, wherein the total amount of betaine amphoteric surfactants in the composition is in the range of 0-75 wt. % of the total amount of amine oxide amphoteric surfactant.

Surprisingly it has been found that the composition according to the invention, comprising a specific amount of at least one food allowed organic acid in combination with a specific amount of at least one specific type of amphoteric surfactant, provides an antibacterial disinfecting agent with good product properties. This composition has the advantage that it can be registered as a disinfectant, but at the same time has sufficient foaming and cleaning ability to be used as a hand soap, body wash or hard surface cleaner disinfectant. Further, the composition does not lead to any use precautions or hazard statements on the product label. Additionally, it has been found that, for a composition with such an attractive profile as regards use precautions and hazard statements, the composition shows a surprisingly high activity against a broad spectrum of bacteria, also after very short contact times. The composition is in particular a disinfectant for skin or mucous membranes. Further advantages of the composition according to the invention and specific embodiments thereof will become clear from the further specification.

The present invention will be discussed in more detail below.

The composition according to the invention comprises 0.1-1 wt. % of each of at least one food allowed organic acid or a salt thereof. The preferred concentration of the food allowed acid or acids is 0.2-1 wt. %, more preferably 0.5-1 wt. % for each of the acids. It may be preferred for the total concentration of food allowed organic acids as described herein to be in the range of 0.2 to 3 wt. %. As indicated above, each individual food allowed organic acid will be present in an amount of at most 1 wt. %.

Food allowed organic acids are organic acids that are officially allowed to be added to food and food preparations for reason of preservation, buffering, acidity regulation, or taste. These organic acids carry an "E-number" in the European Union.

Most preferred food allowed organic acids are carboxylic acids having 3-6 carbon atoms including the carboxylic acid residues. The carboxylic acids may be mono, di or tricarboxylic acids. Preferred acids are citric acid, lactic acid, tartaric acid, malic acid, fumaric acid, adipic acid, or succinic acid. Even more preferred are carboxylic acids with at least one hydroxy group. Most preferred hydroxy carboxylic acids are citric acid, lactic acid, tartaric acid and malic acid. Citric acid, lactic acid and tartaric acid are more preferred and lactic acid is most preferred.

The composition according to the invention comprises 0.1-1 wt. % of each of at least one amine oxide amphoteric surfactant. Preferred amine oxides are alkyldimethylamines, for example decylamine oxide, lauramine oxide, cocamine oxide and myristamine oxide.

In general, the amine oxide amphoteric surfactant has the formula $R1R2R3N^+O^-$, wherein R1 comprises 8 to 18 carbon atoms and R2 and R3 each contain 1-4 carbon atoms. R2 and R3 each preferably contain 1 or 2 carbon atoms. It is preferred for both R2 and R3 to be methyl. It is preferred for R1 to be selected form alkyl groups with 8 to 18 carbon atoms, in particular 10 to 16 carbon atoms, more in particular 10 to 14 carbon atoms. It is preferred for the amine oxide amphoteric surfactant to be selected from C8-C18 dimethyl amine oxides, in particular C10-16 dimethyl amine oxides, more in particular C10-C14 dimethyl amine oxides. It has been found that C10 (decyl) and C12 (dodecyl or lauryl) dimethyl amine oxides show particularly good results. Coco-dimethyl amine oxide, which is a mixture of C10-C18 dimethyl amine oxides also find use in this application.

The preferred concentration for each of the amine oxide amphoteric surfactant or amphoteric surfactants in combination is 0.5-1%, more preferably 0.9-1 wt. %. This preference applies to each individual amine oxide amphoteric surfactant present in the composition.

The composition according to the invention comprises at least one amine oxide amphoteric surfactant, but the presence of a second, third or fourth amphoteric surfactant is not excluded. The concentration of the additional amphoteric surfactant may not exceed the concentration of the first component. In other words, the upper limit of 1 wt. % applies to all amine oxide amphoteric surfactants present in the composition, and to any other amphoteric surfactants, such as amphoteric amines, amphotheric (hydroxyl)sultaines, or amphoteric imino propionates or acetates. For amphoteric betaines other ranges apply.

It may be preferred for the composition according to the invention to comprise at least two amine oxide amphoteric surfactants, e.g., 2 to 6 amine oxide amphoteric surfactants, e.g, two, three, or four, wherein each amine oxide amphoteric surfactant is present in an amount of 0.5-1 wt. %, more preferably 0.9-1 wt. %, and wherein each amine oxide amphoteric surfactant is selected from C8-C18 dimethyl amine oxides, in particular C10-16 dimethyl amine oxides, more in particular C10-C14 dimethyl amine oxides, in particular C10 and C12 dimethyl amine oxides.

It has been found that betaines, even though they are amphoteric surfactants like amine oxides, are not able to achieve the effect of the invention, namely a broad spectrum antibacterial effect after a short contact time. This is in itself surprising, because WO2007/100917 specifically describes a composition comprising a combination of two amphoteric betaines and an amine oxide as antimicrobial agent. Therefore, in the composition of the invention, the total amount of betaine amphoteric surfactants is in the range of 0-75 wt. % of the total amount of amine oxide amphoteric surfactant. In other words, betaine amphoteric surfactants may be present in the composition, but if they are, they are present in an amount which is well below the amount of amine oxide amphoteric surfactant. As it is believed that betaine amphoteric surfactants do not contribute to the effect of the present invention, it is preferred to use them in limited amounts, or not use them at all. Therefore, it is preferred for the total amount of betaine amphoteric surfactants in the composition to be in the range of 0-50 wt. % of the total amount of amine oxide amphoteric surfactant, in particular in the range of 0-25 wt. %, more in particular in the range of 0-10 wt. %. It is particularly preferred for the composition to be essentially free of betaine amphoteric surfactants. The term essentially free means that the compound is present only in such amounts as cannot reasonable be avoided, e.g., due to the presence of contaminants.

Other amphoteric surfactants, e.g., amphoteric amines may also be present in the composition The ranges of 0.1-1 wt. %, preferably 0.5-1 wt. %, more preferably 0.9-1 wt. % apply to each amphoteric surfactant present in the composition, with the exception of betaine amphoteric surfactants.

The present invention is directed to a composition with a limited amount of surfactant, namely at most 8 wt. %, which show high antimicrobial activity in combination with good foaming properties. It may be preferred for the composition to comprise at most 6 wt. % of surfactant. In particular the total amount of surfactant does not exceed 4 wt. %, preferably 3 wt. % and in some embodiments 2 wt. %.

It is furthermore preferred according to the present invention that anionic surfactants are only minimally present, and preferably no anionic surfactant is added to the composition, as this compound does not contribute to the antimicrobial effectiveness of the composition. Therefore, it is preferred for the composition according to the invention to comprise at most 4 wt. % of anionic surfactant, in particular at most 2 wt. %, more in particular at most 1 wt. %.

It is preferred for the composition according to the invention to be essentially free of anionic surfactants. The term essentially free means that the compound is present only in such amounts as cannot reasonable be avoided, e.g., due to the presence of contaminants.

It is furthermore preferred according to the present invention that no phospholipids are added to the composition, as these compounds do not contribute to the antimicrobial effectiveness of the composition. Therefore, it is preferred for the composition according to the invention to comprise at most 2 wt. % of phospholipids, in particular at most 1 wt. %, more in particular at most 0.5 wt. %. It is preferred for the composition according to the invention to be essentially free of phospholipids. The term essentially free means that the compound is present only in such amounts as cannot reasonable be avoided, e.g., due to the presence of contaminants.

It is possible for the composition according to the invention to comprise cationic surfactants. If present, these are generally present in an amount of 0-3 wt. %, in particular 0-2 wt. %, more in particular up to 1 wt. %.

However, as regards biocidally active quaternary ammonium compounds, it is preferred that they are present only at mimumal levels. It is more preferred for the composition according to the invention to be essentially free of quaternary ammonium cationic surfactants, as these compounds have been shown to sometimes cause skin irritation, and may lead antibacterial resistance. If used, these compounds are generally present in an amount of 0-1 wt. %, more in particular 0-0.5 wt. %. It is preferred for the composition according to the invention to be essentially free of quaternary ammonium cationic surfactants. The term essentially free means that the compound is present only in such amounts as cannot reasonable be avoided, e.g., due to the presence of contaminants.

In one embodiment of the present invention, the composition according to the invention is capable of achieving the requirements of EN 1276 (a log reduction upon contacting of at least 5), against bacteria, in particular against one or more of *Escherichia coli*, *Staphylococcus aureus*, *Enterococcus hirae*, and *Pseudomonas aeruginosa*, more in particular against at least two, in particular at least three, more in particular against all four of these organisms, within maximum 5 minutes. In preferred embodiments, this requirement is met within 2 minutes, and in some embodiments more specifically within one minute. In some specific embodiments it has been found that for at least some organisms the requirements of EN 1276 are already met within 30 seconds.

As described before, quaternary ammonium compounds may have adverse skin irritating effects, while triclosan has been found to accumulate within the body, and recent studies have linked triclosan to the development of allergies and disruption of hormone regulation. Because of the potential safety issues associated with triclosan, some consumer groups have called for a ban on its use. Indeed, the hazards of triclosan are reflected in its registration as a pesticide with the Environmental Protection Agency. In view of the aforementioned health concerns, both the Food and Drug Administration and Environmental Protection Agency are currently re-evaluating the safety of triclosan in consumer products. However, despite concerns on triclosan's safety, its use remains widespread due to the compound's superior antibacterial properties. Also polymeric biguanides are widely used in antimicrobial preparations. This group of compounds is recently classed in the European Union as "suspect carcinogenic" and put on the list of CMR-rated substances (Carcinogenic, Mutagenic, Reprotoxic-list).

In another embodiment of this invention a composition is provided that is essentially free of antibacterial active ingredients that are causing antimicrobial resistance, skin irritating or are suspicious. In yet another embodiment, a composition is provided that is essentially free of quaternary ammonium compounds, biguanides, parachlorometaxylenol (PCMX) or triclosan.

Additives are frequently included in cleansing formulations to improve the aesthetic properties of a product. For example, a viscosity enhancing agents may be added to the invention to provide the antibacterial composition with a desired texture and feel. A viscosity enhancing agent may be present in an amount less than about 1 wt %, for example, about 0.9 wt %. Suitable viscosity enhancing agents include, for example, hydroxypropyl guar, seaweed extracts, synthetically modified versions of cellulose and/or starch, propylene glycol alginate, carboxymethyl locust bean gum, carboxymethyl guar, xanthan gum, carboxymethylcellulose, hydroxyethylecellulose, sodium alginate and other salts of alginic acid, carrageenan, gum arabic, gum karaya, gum tragacanth, gum ghatti, guar gum, locust bean gum, and other polysaccharides.

The composition of the invention has a pH of 2-7, preferably a pH of 2-6, more preferably 3-6, most preferably 3-5. Such pH may be maintained, for example, by the acids as described herein or pH buffers. At this pH the amphoteric surfactant will be in its cationic form.

Optionally, preservatives may be present in the invention. The total concentration of preservatives in the composition is optimally less than about 1 wt %, and will at least need to be less than the threshold for the product to receive hazard classification under GHS/CLP guidelines. Examples of suitable preservatives include phenoxyethanol, phenylpropanol, benzoic acid, salicylic acid, furan carboxylic acid, lactates, lactylates, caprylates, caprates, caprylyl glycol, benzyl alcohol, methylchloroisothiazolinone, methylisothiaziolinone, etc. One skilled in the art would understand that other preservatives, including but not limited to those based on carboxylic organic acids such as sorbic acid, or cyclic carboxylic acids such as benzoic acid and salicylic acid may also be used in the liquid cleansing composition according to the invention.

Skin conditioning agents are optionally present in the formulation. Skin conditioning agents improve cosmetic benefits, skin conditioning and skin softening. Examples of skin conditioning agents may include glycerol, carnitine glycerides, polyglycerol, aloe vera, vitamin E, sorbitol, urea, panthenol, hyaluronic acid, allantoin, cationics, polymers, castor oil, lanolin and its derivatives and cetyl alcohol.

Preferably, one or more skin conditioning agents are present in the composition according to the invention, preferably in a concentration of 0.1-6%, in particular in a concentration of 0.1-4 wt. %, preferably in a concentration of 0.1-2 wt. %, more preferably in a concentration of 0.1-1%.

The composition may further optionally comprise organic solvents such as alcohols or glycol ethers.

Other ingredients known in the art to improve the commercial appeal of the product may be present in the invention either alone or in combination. Examples include humectants, fragrances, dyes, and antioxidants, all of which are well-known to a person skilled in the art.

The composition according to the invention may be applied to a hard or soft surface, a human or animal skin, a mucous membrane or air to eliminate microorganisms. A cleansing composition according to the invention may be applied in a similar fashion to additional areas of the body or other surfaces to reduce bacterial contamination.

The composition of the present invention can be used for disinfection substrates, in particular skin or mucous membranes, and/or for sanitization thereof, preferably for disinfection and/or sanitization of hands, face, intimate areas, hair and arms. Next to being suitable for use on the skin the composition also may be used for other disinfecting and/or sanitizing purposes such as for use on hard surfaces.

In another aspect the invention relates to a method to reduce the bacteria population on a surface, e.g., the gram-negative bacteria population on a hard or soft surface, a human or animal skin or mucous membrane by contacting the substrate for at least 30 seconds with the composition according the present invention.

It will be clear to the skilled person that the various embodiments and preferences describes herein can be combined, unless they are presented as mutually excluding alternatives.

The invention will be elucidated by the following examples, without being limited thereto or thereby.

EXAMPLES

Starting Materials:
The following products are used in the present examples:

| | |
|---|---|
| Akyposoft 100 BVC | Sodium Laureth-11 Carboxylate & Laureth-10 |
| Dehyton AB30 | Coco-betaine |
| Dermosoft Octiol | Caprylyl Glycol |
| Jaguar HP 105 | Hydroxypropyl Guar |
| Lipoxol 400 | Polyethyleneglycol (n = 4) |
| Mackam CAB-818 | Cocoamidopropyl betaine |
| Mackam CB-35 | Coco-betaine |
| Mackamine 065 | Decylamine oxide (C10) |
| Mackamine CS | Cocoamine oxide (C10-C18) |
| Mackamine LA | laurylamine oxide (C12) |
| Mackamine MY | Myristylamine oxide (C14) |
| Oxidet DM-20 | laurylamine oxide (C12) |
| Oxidet DM-4 | Myristylamine oxide (C14) |
| plantacare 818 | Coco-glucoside |
| Sensiva SC 50 | Ethylhexylglycerine |
| texapon N70 | Sodium Laureth Sulfate (2EO) |
| Texapon T42 | Triethanolamine Lauryl Sulfate |

Example 1

Two series of formulas have been prepared and tested for antimicrobial efficacy according the EN 1276 suspension test.

The first series (Table 1), numbered 1-16 are prepared according the invention. These samples contain a food allowed organic acid and an amphoteric surfactant in a set-up that could be used as an antimicrobial hand soap, or body wash, containing other ingredients, whereby some formulations contain preservatives and skin conditioners.

The second series, numbered 17-25 (Table 2) are prepared as hand soaps or body wash, with a different surfactant base, and were prepared not according the invention. All samples were formulated containing salts of lauryl ether sulfate, a surfactant very commonly used in hard surface compositions, hand soaps and shampoos.

From the efficacy data in Table 3 it is clearly shown that samples 1-16, which are all prepared according the invention, show very low remaining organisms of all tested species, after 3 contact times. The start suspension of the micro-organisms was for $E\ coli$ $1.3 \times 10^7$, for $S.\ aureus$ $4 \times 10^7$ and for $E.\ hirae$ $1.8 \times 10^7$ cfu/ml. This results show high antibacterial effect of the compositions according to the invention.

In the EN 1276, 1 ml of micro-organism suspension (of at least $1 \times 10^6$ cfu/ml) and 1 ml of interfering substance (soil) are added to 8 ml of test product, mixed and left for the contact time. After the contact time, 1 ml of mixture is added to 9 ml of neutralizer liquid, neutralizing the biocidal effect of the product. The product is plated out on a growth medium and incubated for 24 hours at 37 C. After 24 hours the plate is counted and reduction between the start suspension (cfu/ml) and the numbers on the plate (cfu/ml) is calculated. A minimum of log 5 is required.

With 2 dilution steps lost, a count of zero at the plate results in a >log 5 reduction in 5 minutes contact time. For example samples 1-16 have a >log 5 reduction at 5 minutes for all 3 organisms, while most having a >log 5 result within only 3 minutes and some already at 1 minute. The formula's not according the invention (no's 17-25), have much higher counts on the plate and are therefore substantially less active.

TABLE 1

| Formula's 1-16 according to the invention (data in wt./wt.) | | | | | | | | | | | | | | | | |
|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 |
| Deionized water | pm | pm | pm | pm | pm | pm | pm | pm | pm | pm | pm | pm | pm | pm | pm | pm |
| Sodium Benzoate | | 0.6 | | | 0.6 | | 0.6 | | | | | | | | | |
| Benzoic acid | | | | | | 0.6 | | 0.6 | | | | | | | | |
| Sodium Salicylate | | | | 0.4 | | | | | | | 0.4 | | | | | |
| Salicylic acid | | | | | | | | | | 0.4 | | | | | | |
| Mackamine MY | 0.95 | | 0.95 | 0.95 | 0.95 | 0.95 | 0.95 | 0.95 | 0.95 | 0.95 | 0.95 | 0.95 | 0.95 | 0.95 | 0.95 | 0.95 |
| Mackamine LA | 0.95 | 0.95 | 0.95 | 0.95 | 0.95 | 0.95 | 0.95 | 0.95 | 0.95 | 0.95 | 0.95 | 0.95 | 0.95 | 0.95 | 0.95 | |
| Mackamine CS | | | 0.95 | 0.95 | 0.95 | | 0.95 | | 0.95 | 0.95 | | | 0.95 | | | |
| Mackamine 065 | | | | | | 0.95 | | | | | | | 0.95 | | 0.95 | 0.95 |
| Mackam CAB-818 | | | | | | | | | | | | | | | | |
| Mono Propylene Glycol | 2.00 | 2.00 | 2.00 | 2.00 | 2.00 | 2.00 | 2.00 | 2.00 | 2.00 | 2.00 | 2.00 | 2.00 | 2.00 | 2.00 | 2.00 | 2.00 |
| Lipoxol 400 | 0.50 | 0.50 | 0.50 | 0.50 | 0.50 | 0.50 | 0.50 | 0.50 | 0.50 | 0.50 | 0.50 | 0.50 | 0.50 | 0.50 | 0.50 | 0.50 |
| Jaguar HP 105 | | | | | | | | | | | | 1.00 | 1.00 | | | |
| Tartaric acid | 0.30 | 0.30 | 0.40 | 0.30 | 0.80 | 0.80 | 0.40 | | 0/70 | 0.55 | 0.60 | 0.30 | | 0.30 | 0.30 | 0.30 |
| Phosphoric acid | | | | | | | | 0.25 | | | | | 0.10 | | | |
| Phenoxyethanol | | | | | | | 1.00 | | | | | | | 0.90 | 0.90 | |
| Sensiva SC 50 | | | | | | | | 0.80 | | 0.80 | | | 0.50 | | | |
| Dermosoft Octiol | | | | | | | | 0.80 | | | | | | | | |
| Lactic acid | 0.95 | 0.95 | 0.95 | 0.95 | 0.95 | 0.90 | 0.95 | 0.95 | 0.95 | 0.95 | 0.80 | 0.50 | 0.70 | 0.90 | 0.90 | 0.90 |
| NaOH 30% | 0.06 | | | | 0.10 | | | | | | | | 0.10 | 0.32 | 0.12 | 0.38 |
| Citric acid | | 0.67 | 0.90 | 0.66 | | 0.40 | 0.90 | 0.95 | 0.80 | 0.85 | 0.40 | | 0.95 | | | |
| pH | 3.5 | 3.5 | 3.5 | 3.5 | 3.5 | 3.5 | 3.5 | 3.5 | 3.5 | 3.5 | 3.5 | 3.5 | 3.5 | 4.5 | 4.5 | 5.0 |

TABLE 2

| Formula's 17-25 not according to the invention (data in wt./wt.) | | | | | | | | | |
|---|---|---|---|---|---|---|---|---|---|
| | 17 | 18 | 19 | 20 | 21 | 22 | 23 | 24 | 25 |
| Deionized water | pm | pm | pm | pm | pm | pm | pm | pm | pm |
| Sodium Benzoate | | | | | | | | | |
| Sodium Salicylate | | | | | | | | | |
| Mackamine LA | 0.95 | | | | | | | 0.95 | |
| Mackamine MY | | | | | | | | | 0.95 |
| texapon N70 | | 0.95 | 0.95 | | 0.95 | | 0.95 | | |
| Mackam CAB 818 | 0.9 | | | | | | | | |
| Texapon T42 | | | | 0.95 | | | | | |
| plantacare 818 | | | 0.95 | 0.95 | | | | | |
| Akyposoft 100 BVC | | | | | | 1.40 | | | |
| Mono Propylene Glycol | 2.00 | 2.00 | 2.00 | 2.00 | 2.00 | 2.00 | 2.00 | 2.00 | 2.00 |
| Lipoxol 400 | 1.00 | 1.00 | 1.00 | 1.00 | 1.00 | 1.00 | 1.00 | 1.00 | 1.00 |
| Lactic acid | 0.9 | 0.95 | 0.95 | 0.95 | 0.95 | 0.95 | | | |
| NaOH 30% | 0.1 | 0.64 | 0.64 | 0.65 | 0.57 | 0.50 | | | |
| Phosphoric acid | | | | | | | | 0.10 | 0.10 |
| Citric acid | | | 0.06 | | | | | 0.40 | |
| pH | 3.5 | 3.5 | 3.5 | 3.5 | 3.5 | 3.5 | 3.5 | 3.5 | 3.5 |

TABLE 3

| Microbial survival | | | | | | | | | |
|---|---|---|---|---|---|---|---|---|---|
| | E. coli (suspension 1.3 × 10$^7$ cfu/ml) | | | S. aureus (suspension 4 × 10$^7$ cfu/ml) | | | E. hirae (suspension 1.8 × 10$^7$ cfu/ml) | | |
| | 1 min | 3 min | 5 min | 1 min | 3 min | 5 min | 1 min | 3 min | 5 min |
| 1 | 3 | 0 | 0 | 0 | 0 | 0 | 1 | 0 | 0 |
| 2 | 0 | 0 | 0 | 0 | 0 | 0 | 7 | 2 | 0 |
| 3 | 0 | 1 | 0 | 0 | 0 | 0 | 72 | 2 | 0 |
| 4 | 0 | 0 | 0 | 0 | 0 | 0 | 0 | 1 | 0 |
| 5 | 0 | 0 | 0 | 0 | 0 | 0 | 0 | 0 | 0 |
| 6 | 0 | 1 | 0 | 7 | 1 | 0 | 36 | 0 | 0 |
| 7 | 1 | 0 | 0 | 0 | 0 | 0 | 1 | 0 | 0 |

TABLE 3-continued

| | Microbial survival | | | | | | | | |
|---|---|---|---|---|---|---|---|---|---|
| | E. coli (suspension 1.3 × 10^7 cfu/ml) | | | S. aureus (suspension 4 × 10^7 cfu/ml) | | | E. hirae (suspension 1.8 × 10^7 cfu/ml) | | |
| | 1 min | 3 min | 5 min | 1 min | 3 min | 5 min | 1 min | 3 min | 5 min |
| 8 | 0 | 0 | 0 | 0 | 0 | 0 | 0 | 0 | 0 |
| 9 | 0 | 1 | 0 | 0 | 0 | 0 | 1 | 0 | 0 |
| 10 | 0 | 0 | 0 | 0 | 0 | 0 | 4 | 3 | 0 |
| 11 | 0 | 1 | 0 | 0 | 0 | 0 | 3 | 0 | 0 |
| 12 | 0 | 3 | 0 | 186 | 0 | 0 | 1 | 0 | 0 |
| 13 | 0 | 0 | 0 | 1 | 0 | 0 | 38 | 0 | 0 |
| 14 | 0 | 0 | 0 | 0 | 0 | 0 | 0 | 0 | 0 |
| 15 | 0 | 0 | 0 | 0 | 0 | 0 | 0 | 0 | 0 |
| 16 | 0 | 0 | 0 | 0 | 0 | 0 | 0 | 0 | 0 |
| 17 | 120 | 10 | 0 | 290 | 0 | 0 | 54 | 5 | 0 |
| 18 | >1000 | >1000 | 0 | >1000 | 231 | 71 | >1000 | 0 | 0 |
| 19 | >1000 | >1000 | >1000 | >1000 | >1000 | >1000 | >1000 | >1000 | >1000 |
| 20 | >1000 | >1000 | 0 | >1000 | >1000 | 28 | >1000 | 28 | 0 |
| 22 | >1000 | >1000 | >1000 | >1000 | >1000 | >1000 | >1000 | >1000 | >1000 |
| 23 | >1000 | >1000 | >1000 | >1000 | >1000 | >1000 | >1000 | >1000 | >1000 |
| 24 | >1000 | >1000 | >1000 | >1000 | >1000 | >1000 | >1000 | >1000 | >1000 |
| 25 | >1000 | 23 | 0 | >1000 | >1000 | >1000 | >1000 | >1000 | 85 |
| 26 | >1000 | 210 | 0 | >1000 | >1000 | >1000 | >1000 | >1000 | 123 |

As can be seen from table 3, compositions 1 through 16 according to the invention show high efficacy against *E. coli, S. aureus*, and *E. hirae*. In contrast, compositions 17-26 do not show high activity against these three organisms.

Example 2

A comparative composition was prepared in accordance with the teachings of WO2007/100917. Table 4 provides the composition and the results of activity tests according to EN 1276 mentioned above.

TABLE 4

| | Example A - Comparative 1 |
|---|---|
| Alkyl betaine mixture comprising about 50 wt. % C12 betaine, about 20 wt. % C14 betaine, and the balance other C8-C18 betaines. | 0.45 |
| Cocamidopropyl amine oxide | 0.45 |
| Citric acid | 0.8 |
| pH | 4.85 |
| Time to a complete kill | |
| S. aureus | 3 minutes |
| E. hirae | >3 minutes |
| E. coli | >3 minutes |
| P. aeruginosa | 1 minute |

Example 3

Compositions according to the invention were prepared and tested as described in Example 2. Table 5 shows the compositions and the results.

TABLE 5

| | Example B - invention 1 | Example C - invention 2 | Example D - invention 3 | Example E - invention 4 |
|---|---|---|---|---|
| Cocamidopropyl amine oxide | 0.9 | | | |
| Myristyldimethyl amine oxide | | 0.9 | 0.9 | 0.9 |
| Lauryldimethyl amine oxide | | 0.9 | 0.9 | 0.9 |
| Decyldimethyl amine oxide | | | 0.9 | 0.9 |
| Citric acid | | | 0.8 | |
| Lactic acid | 0.8 | 0.8 | | 0.8 |
| pH | 4.85 | 4.85 | 4.85 | 4.85 |
| Time to a complete kill | | | | |
| S. aureus | 30 sec | 30 sec | 1 min | 30 sec |
| E. hirae | 1 min | 30 sec | 30 sec | 30 sec |
| E. coli | 1 min | 1 min | 1 min | 1 min |
| P. aeruginosa | 30 sec | 30 sec | 30 sec | 30 sec |

As can be seen from a comparison between Tables 4 and 5, the compositions according to the present invention show substantially better results than a composition in accordance with the teachings of WO2007/100917.

Example 4

A formula according to the invention was tested in a European controlled suspension test EN 1276 in soiled conditions. The composition of the formula was as follows:

TABLE 6

| | |
|---|---|
| Decyl dimethyl amine oxide | 0.9% |
| Lauryl dimethyl amine oxide | 0.9% |
| Myristyl dimethyl amine oxide | 0.9% |
| Monopropylene glycol | 2.0% |
| PEG-400 | 0.5% |
| Tartaric acid | 0.3% |
| Lactic acid | 0.9% |
| Sodium hydroxide | 0.2% |
| Water | pm |
| pH | 4.5 |

The composition passed the requirements of the norm (greater than log 5 reduction) for each of the organisms with the following contact times for each organism:

| | |
|---|---|
| E. coli | 30 sec |
| E. hirae | 30 sec |
| S. aureus | 60 sec |
| P. aeruginosa | 60 sec |

Furthermore, this formula was tested according the stringent European hand washing norm EN 1499 and passed in 15 seconds exposure time.

Furthermore, this formula was tested in a 48 hours occluded skin patch test to test skin tolerance and was found to cause no measurable irritation after 48 hours exposure with 30 subjects.

These results clearly show that a composition according to the invention, which holds no hazard classification according the CLP regulations, is capable of meeting the stringent requirements of EN 1276 and EN 1499 while at the same time it is so mild that the occluded skin patch test showed no measurable irritation after 48 hours exposure with 30 subjects.

Example 5

The compositions presented in Table 7 below were all tested in a controlled European suspension test EN 1276 against E. coli, S. aureus, and E. hirae. All samples passed the test against E coli and E. hirae in 30 seconds and against S. aureus in 60 seconds. The high logarithmic reductions (>log 5) within very short exposure times evidences the very high disinfection power of these solutions.

| | Labcode | | | | | | |
|---|---|---|---|---|---|---|---|
| | 3-15C | 3-15D | 3-15H | 3-15I | 3-15J | 3-15L | 3-15M |
| Deionized water | 93.50 | 92.53 | 92.50 | 92.45 | 92.80 | 92.90 | 91.84 |
| Mackamine MY | 0.90 | 0.90 | 0.90 | 0.90 | 0.90 | 0.90 | 0.90 |
| Mackamine LA | 0.90 | 0.90 | 0.90 | 0.90 | 0.90 | 0.90 | 0.90 |
| Mackamine 065 | 0.90 | 0.90 | 0.90 | 0.90 | 0.90 | 0.90 | 0.90 |
| Mackamine CS | | | | | | | 0.90 |
| Mono Propylene Glycol | 2.00 | 2.00 | 2.00 | 2.00 | 2.00 | 2.00 | 2.00 |
| Dermosoft GMCY | | | 1.00 | | | | |
| Geogard Ultra | | | | 1.00 | | | |
| Benzoic Acid | | | | | 0.70 | | 0.70 |
| Potassium Sorbate | | | | | | 0.60 | |
| Lipoxol 400 | 0.50 | 0.50 | 0.50 | 0.50 | 0.50 | 0.50 | 0.50 |
| Tartaric acid | 0.30 | 0.30 | 0.30 | 0.30 | 0.30 | 0.30 | 0.30 |
| Phenoxyethanol | | 0.95 | | | | | |
| Lactic acid | 1.00 | 1.00 | 1.00 | 1.00 | 1.00 | 1.00 | 1.00 |
| Citric acid | pm | 0.02 | pm | 0.05 | pm | pm | 0.06 |
| NaOH 30% | | | | | | | |
| NaOH | 0.17 | 0.18 | 0.18 | 0.28 | 0.19 | 0.09 | 0.23 |
| pH | 4.8 | 4.5 | 5.0 | 4.5 | 4.0 | 4.0 | 5.0 |

None of the above compositions is hazard classified according the CLP or GHS product labeling regulations.

Example 6

Compositions according to the invention were prepared and tested as described in Example 2. Table 8 shows the compositions and the results.

TABLE 8

| | Inv 6.1 | Inv 6.2 | Inv 6.3 | Inv 6.4 | Inv 6.5 |
|---|---|---|---|---|---|
| Deionized water | | | | | |
| Myristyl dimethyl amine oxide | 0.90 | 0.90 | 0.90 | 0.90 | 0.90 |
| Lauryl dimethyl amine oxide | 0.90 | 0.90 | 0.90 | 0.90 | 0.90 |
| Decyldimethylamine oxide | | | 0.90 | | |
| Cocamidopropylbetaine | | | | 0.90 | 0.90 |
| Mono Propylene Glycol | 2.00 | 2.00 | 2.00 | 2.00 | 2.00 |
| Lipoxol 400 | 0.50 | 0.50 | 0.50 | 0.50 | 0.50 |
| Tartaric acid | 0.30 | 0.30 | 0.30 | 0.30 | 0.30 |
| Phenoxyethanol | | 0.95 | 0.95 | 0.95 | |
| Lactic acid | 0.9 | 0.9 | 0.9 | 0.9 | 0.9 |
| Citric acid | 0.3 | 0.3 | 0.8 | 1.00 | 1.00 |
| NaOH 30% | 0.77 | 0.77 | 0.77 | 0.77 | 0.77 |
| NaOH | | | | | |
| pH | 4.0 | 4.0 | 4.0 | 4.0 | 4.0 |
| Time to a complete kill | | | | | |
| S. aureus | 1 min | 30 sec | 30 sec | 1 min | 3 min |
| E. coli | 30 sec | 30 sec | 30 sec | 1 min | >3 min |

All compositions in this table are according to the broadest aspect of the invention. It can be seen, however, that compositions 6.4 and 6.5, which contain a betaine compound perform less well than, respectively, compositions 6.2 and 6.1, which are the same, but which do not contain the betaine compound. This supports the preference in the present invention for compositions wherein the total amount of betaine amphoteric surfactants is in the range of 0-25 wt. % of the total amount of amine oxide amphoteric surfactant, in particular in the range of 0-10, or wherein the composition is essentially free of betaine amphoteric surfactants.

The invention claimed is:

1. An antimicrobial disinfecting composition comprising: a) 0.1-1 wt. % of each of at least one food allowed organic acid or a salt thereof wherein the at least one food allowed organic acid comprises at least one C3-C6 carboxylic acid, and wherein the at least one C3-C6 carboxylic acid is selected from the group consisting of citric acid, lactic acid, tartaric acid, malic acid, fumaric acid, adipic acid and succinic acid; b) 0.1-1 wt. % of each of at least one amine oxide amphoteric surfactant, the amine oxide amphoteric surfactant having a formula R1R2R3N+O—, wherein R1 is an alkyl group that contains 8 to 18 carbon atoms and R2 and R3 are each an alkyl group that contains 1-4 carbon atoms, and wherein if betaine amphoteric surfactants are included, a total amount of the betaine amphoteric surfactants in the composition is 75 wt. % or less of a total amount of the amine oxide amphoteric surfactant in the composition, the composition having a total surfactant content which does not exceed 8 wt. %, the composition having a pH in a range of from 2 to 6, the composition including less than 1 wt. % quaternary ammonium compounds, and the composition not including peroxides or triclosan.

2. The composition of claim 1, wherein if betaine amphoteric surfactants are included, the total amount of betaine amphoteric surfactants in the composition is in the range of 0-50 wt. % of the total amount of amine oxide amphoteric surfactant in the composition.

3. The composition of claim 1, wherein the composition is essentially free of betaine amphoteric surfactants.

4. The composition of claim 1, wherein the composition comprises at least two amine oxide amphoteric surfactants.

5. The composition of claim 1, wherein the C3-C6 carboxylic acid is selected from a hydroxy carboxylic acid.

6. The composition of claim 1, wherein the C3-C6 carboxylic acid is selected from citric acid, lactic acid and tartaric acid.

7. The composition of claim 1, which in addition contains 0.1%-6% of at least one skin conditioning agent.

8. The composition of claim 1, that is capable of achieving a log reduction upon contacting of at least 5, against bacteria.

9. The composition of claim 1, wherein the composition comprises at most 6 wt. % of surfactant.

10. The composition of claim 1, which comprises at most 4 wt. % of anionic surfactant.

11. The composition of claim 1 which is essentially free of quaternary ammonium compounds, parachlorometaxylenol (PCMX) and biguanides.

12. The composition of claim 1 for disinfecting substrates.

13. Method to reduce bacteria on a hard or soft surface, a human or animal skin or mucous membrane by contacting for at least 30 seconds with the composition according to claim 1.

14. The method of claim 13, wherein the bacteria population is a gram-negative bacteria population.

15. The composition of claim 1, wherein the composition is essentially free from phospholipids.

16. The composition of claim 1, wherein in the amine oxide amphoteric surfactant having the formula $R1R2R3N^+O^-$, R2 and R3 are each an alkyl group containing 1 or 2 carbon atoms.

17. The composition of claim 1, wherein in the amine oxide amphoteric surfactant having the formula $R1R2R3N^+O^-$, R2 and R3 are both methyl.

18. The composition of claim 1, wherein in the amine oxide amphoteric surfactant having the formula $R1R2R3N^+O^-$, R1 is an alkyl group with 10 to 16 carbon atoms.

19. The composition of claim 1, wherein in the amine oxide amphoteric surfactant having the formula $R1R2R3N^+O^-$, R1 is an alkyl group with 10 to 14 carbon atoms.

20. The composition of claim 1, wherein the composition achieves the requirement of EN 1276 within 5 minutes against one or more bacteria selected from the group consisting of *Escherichia coli, Staphylococcus aureus, Enterococcus hirae*, and *Pseudomonas aeruginosa*.

* * * * *